United States Patent
Dannenberg

(10) Patent No.: US 7,041,694 B1
(45) Date of Patent: May 9, 2006

(54) CYCLOOXYGENASE-2 INHIBITION

(75) Inventor: Andrew J. Dannenberg, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1038 days.

(21) Appl. No.: 09/554,604

(22) PCT Filed: Dec. 7, 1998

(86) PCT No.: PCT/US98/25206

§ 371 (c)(1),
(2), (4) Date: May 31, 2000

(87) PCT Pub. No.: WO99/30721

PCT Pub. Date: Jun. 24, 1999

Related U.S. Application Data

(60) Provisional application No. 60/069,955, filed on Dec. 17, 1997.

(51) Int. Cl.
*A61K 31/415* (2006.01)
*A61K 31/425* (2006.01)

(52) U.S. Cl. .................. 514/395; 514/370; 514/372

(58) Field of Classification Search ............ 514/395, 514/372, 370
See application file for complete search history.

(56) References Cited

U.S. PATENT DOCUMENTS

| | | | |
|---|---|---|---|
| 5,436,265 A | 7/1995 | Black et al. ............... 514/420 |
| 5,466,823 A | 11/1995 | Talley et al. ............. 548/377.1 |
| 5,474,995 A | 12/1995 | Ducharme et al. .......... 514/241 |
| 5,510,368 A | 4/1996 | Lau et al. ................. 514/419 |
| 5,521,213 A | 5/1996 | Prasit et al. .............. 514/443 |
| 5,552,422 A | 9/1996 | Gauthier et al. ............ 514/368 |
| 5,593,992 A | 1/1997 | Adams et al. ........... 514/235.8 |
| 5,593,994 A | 1/1997 | Batt et al. ................. 514/252 |
| 5,596,008 A | 1/1997 | Lee ......................... 514/347 |
| 5,604,253 A | 2/1997 | Lau et al. ................. 514/415 |
| 5,604,260 A | 2/1997 | Guay et al. ............... 514/605 |
| 5,616,458 A | 4/1997 | Lipsky et al. ................ 435/4 |
| 5,616,601 A | 4/1997 | Khanna et al. ............. 514/399 |
| 5,633,272 A | 5/1997 | Talley et al. ............... 514/378 |
| 5,639,780 A | 6/1997 | Lau et al. ................. 514/419 |
| 5,643,933 A | 7/1997 | Talley et al. ............... 514/372 |
| 6,048,850 A | 4/2000 | Young et al. .............. 514/183 |
| 6,172,096 B1 * | 1/2001 | Gregory ................... 514/395 |

FOREIGN PATENT DOCUMENTS

WO   WO 97/29776   * 8/1997

OTHER PUBLICATIONS

Seibert et al. CAPLUS Abstract, AN 1998:369098, 1997.*
Jeng et al. "Secondary Biliary Cirrhosis A Limiting Factor in the Treatment of Hepatolithiasis" *Arch Surg* vol. 124 pp. 1301-1305, 1989.*
Hurizinga et al. "Chronic Pancreatitis with Biliary Obstruction" *Annals of the Royal College of Surgeons of England* vol. 74 pp 119-125, 1992.*
Haslam, E., "Protection of Phenols and Catechols" in Protective Groups in Organic Chemistry, McOmie, J. F. W., editor, Plenum Press, New York (1973).
Dinchuk, J. E., Nature 378, 406-409 (1995).
Nanji, A. A., et al., Gastroenterology 112, 943-951 (1997).
Branca, A., et al., Derwent Abstract of WO 9639144 A1, AN 97-042830.
Penning, T. D., et al., HCAPLUS Abstract AN 1997:231026 of J. Med. Chem. 1997, 40(9), 1347-1365.
Nanji A. A., et al., Hepatology 26(6), 1538-1543 (1997).
Denda, A., et al., Carcinogenesis 18, 1921-1930 (1997).
Albrecht, C., et al., Hepatology 26, No. 4, Part 2, 333A (Abstract 818) (1997).

* cited by examiner

*Primary Examiner*—Shengjun Wang
(74) *Attorney, Agent, or Firm*—Bacon & Thomas, PLLC

(57) ABSTRACT

Selective inhibitors of cyclooxygenase-2 are used to treat liver disease and in combination with anti-viral drugs to treat virus-caused liver disorders. Selective inhibitors of cyclooxygenase-2 which also inhibit the synthesis of cyclooxygenase-2 improve over the efficacy of conventional selective inhibitors of cyclooxygenase-2 in the treatment of inflammatory conditions, Alzheimer's disease and cancer.

4 Claims, No Drawings

CYCLOOXYGENASE-2 INHIBITION

CROSS-REFERENCE TO RELATED APPLICATIONS

This application is a 371 of PCT/US98/25206 filed Dec. 7, 1998 which claims the benefit of U.S. Provisional Application No. 60/069,955 filed Dec. 17, 1997.

TECHNICAL FIELD

One invention herein is directed to an expansion of the use of selective inhibitors of cyclooxygenase-2. A different invention herein is directed to cyclooxygenase-2 inhibitors with antioxidant properties.

BACKGROUND OF THE INVENTION

Substantial research is currently being carried out to develop selective inhibitors of cyclooxygenase-2, i.e., agents which selectively inhibit cyclooxygenase-2 in preference to cyclooxygenase-1, so as to obtain the anti-inflammatory effect of cyclooxygenase-2 inhibition without the gastrointestinal side effects, e.g., peptic ulcer disease, that occur when cyclooxygenase-1 is also inhibited. Commonly used nonsteroidal anti-inflammatory drugs inhibit both cyclooxygenase-2 and cyclooxygenase-1, and the aforementioned side effects detract from their usefulness.

The focus of the research has been on synthesis of new compounds providing selective inhibition of cyclooxygenase-2 for use for treating certain inflammatory conditions, especially arthritis. The focus has not been on developing new methods of treatment, i.e., on treating conditions not heretofore considered as appropriately treatable with cyclooxygenase-2 inhibitors. The focus has not been on developing compounds with desirable functions in addition to enzyme inhibition.

Heretofore, it was considered that cyclooxygenase inhibitors could cause liver injury and for that reason liver disease was not considered as one of the conditions that was treatable by selective inhibitors of cyclooxygenase-2.

SUMMARY OF THE INVENTION

One embodiment herein, sometimes referred to hereinafter as the first embodiment herein, is directed to a method of treating a patient with liver disease comprising administering to said patient a cyclooxygenase-2 inhibiting amount of a selective inhibitor of cyclooxygenase-2. Most liver diseases are treated with minimal success. There is no effective treatment for alcoholic liver injury. Although chronic hepatitis C affects millions of individuals, interferon therapy is effective in eradicating the virus in a relatively small percentage of patients, and in patients where the virus is not eradicated, the condition can progress to cirrhosis requiring liver transplantation. Invention in the method of treatment herein resides in the realization that the anti-inflammatory properties of selective cyclooxygenase-2 inhibitors will provide a net benefit in treating liver disease and the only effective treatment in many cases. This represents a major advance. Even considering just the ability to delay the progression of cirrhosis, the aforedescribed treatment method has enormous clinical implications.

A second embodiment herein is directed to a method of treating a patient with a virus-caused liver disease comprising administering to said patient a cyclooxygenase-2 inhibiting amount of a selective inhibitor of cyclooxygenase-2 and therapeutic amount(s) of anti-viral drug(s) where the cyclooxygenase-2 inhibitor is an adjunct to anti-viral therapy to increase the effectiveness thereof. In this embodiment, the treatment with a selective inhibitor of cyclooxygenase-2 is considered to cause a decrease in the synthesis of immunosuppressive eicosanoids, thereby augmenting anti-viral therapy.

A third embodiment herein is directed to selective inhibitor of cyclooxygenase-2 which directly inhibits the enzyme cyclooxygenase-2 and which also inhibits the synthesis of the cyclooxygenase-2 protein and which has antioxidant properties.

The term "selective inhibitor of cyclooxygenase-2" is used herein to mean compound which selectively inhibits cyclooxygenase-2 in preference to cyclooxygenase-1 and particularly compound for which the ratio of the $IC_{50}$ concentration (concentration inhibiting 50% of activity) for cyclooxygenase-1 to the $IC_{50}$ concentration for cyclooxygenase-2 is greater than 1. Such ratio is readily determined by assaying for cyclooxygenase-2 activity and assaying for cyclooxygenase-1 activity by the methods set forth at column 39, line 55—column 40, line 36 of Talley et al. U.S. Pat. No. 5,633,272, which is incorporated herein by reference, and from the resulting data obtaining a ratio of $IC_{50}$s.

DETAILED DESCRIPTION

We turn now to the embodiment herein directed to a method of treating a patient with a liver disease comprising administering to said patient a cyclooxygenase-2 inhibiting amount of a selective inhibitor of cyclooxygenase-2.

The liver diseases treated herein comprise inflammatory liver disorders and include, for example, chronic viral hepatitis B, chronic viral hepatitis C, alcoholic liver injury, primary biliary cirrhosis, autoimmune hepatitis, nonalcoholic steatohepatitis, and liver transplant rejection.

The selective inhibitors of cyclooxygenase-2 are preferably those where the ratio of the $IC_{50}$ concentration for cyclooxygenase-1 to the $IC_{50}$ concentration for cyclooxygenase-2 is 5 or more, very preferably 100 or more.

Selective inhibitors of cyclooxygenase-2 include the following compounds:

(1) 4-[5-(4-Chlorophenyl)-3-(trifluoromethyl)-1H-pyrazol-1-yl]benzenesulfonamide
(2) 4-[5-(4-Bromophenyl)-3-(trifluoromethyl)-1H-pyrazol-1-yl]benzenesulfonamide
(3) 4-[5-(3-Chlorophenyl)-3-(trifluoromethyl)-1H-pyrazol-1-yl]benzenesulfonamide
(4) 4-[5-(4-Methylphenyl)-3-(trifluoromethyl)-1H-pyrazol-1-yl]benzenesulfonamide
(5) 4-[5-(2-Chlorophenyl)-3-(trifluoromethyl)-1H-pyrazol-1-yl]benzenesulfonamide
(6) 4-[5-(4-Trifluoromethylphenyl)-3-(trifluoromethyl)-1H-pyrazol-1-yl]benzenesulfonamide
(7) 4-[5-(4-Fluorophenyl)-3-(trifluoromethyl)-1H-pyrazol-1-yl]benzenesulfonamide
(8) 4-[5-Phenyl-3-(trifluoromethyl)-1H-pyrazol-1-yl]benzenesulfonamide
(9) 4-[5-(4-Methoxyphenyl)-3-(trifluoromethyl)-1H-pyrazol-1-yl]benzenesulfonamide
(10) 4-[5-(4-Trifluoromethoxyphenyl)-3-(trifluoromethyl)-1H-pyrazol-1-yl]benzenesulfonamide
(11) 4-[5-(2-Methylphenyl)-3-(trifluoromethyl)-1H-pyrazol-1-yl]benzenesulfonamide
(12) 4-[5-(4-Chlorophenyl)-3-(difluoromethyl)-1H-pyrazol-1-yl]benzenesulfonamide

(13) 4-[4-(Aminosulfonyl)phenyl]-5-(4-chlorophenyl)-1H-pyrazol-3-carboxylate
(14) 4-[4-(Aminosulfonyl)phenyl]-5-(4-chlorophenyl)-1H-pyrazol-3-carboxamide
(15) 4-[5-(4-[Methylthio]phenyl)-3-(difluoromethyl)-1H-pyrazol-1-yl]benzenesulfonamide
(16) 4-[5-(4-[Methylsulfonyl]phenyl)-3-(difluoromethyl)-1H-pyrazol-1-yl]benzenesulfonamide
(17) 4-[5-(2,4-[Difluoro]phenyl)-3-(trifluoromethyl)-1H-pyrazol-1-yl]benzenesulfonamide
(18) 4-[5-(2,6-[Difluoro]phenyl)-3-(trifluoromethyl)-1H-pyrazol-1-yl]benzenesulfonamide
(19) 4-[5-(4-Cyanophenyl)-3-(trifluoromethyl)-1H-pyrazol-1-yl]benzenesulfonamide
(20) 4-[5-(4-Chlorophenyl)-3-(heptafluoropropyl)-1H-pyrazol-1-yl]benzenesulfonamide
(21) 4-[5-(4-Chlorophenyl)-3-(chloro-difluoromethyl)-1H-pyrazol-1-yl]benzenesulfonamide
(22) 4-[5-(4-Chlorophenyl)-3-(pentafluoroethyl)-1H-pyrazol-1-yl]benzenesulfonamide
(23) 4-[5-(4-Biphenyl)-3-(difluoromethyl)-1H-pyrazol-1-yl]benzenesulfonamide
(24) 4-[5-(4-Pyrazinyl)-3-(difluoromethyl)-1H-pyrazol-1-yl]benzenesulfonamide
(25) 4-[5-(5-Chloro-2-thienyl)-3-(difluoromethyl)-1H-pyrazol-1-yl]benzenesulfonamide
(26) 4-[5-(4-Morpholino)phenyl)-3-(difluoromethyl)-1H-pyrazol-1-yl]benzenesulfonamide
(27) 4-[5-(1-Cyclohexyl)-3-(difluoromethyl)-1H-pyrazol-1-yl]benzenesulfonamide
(28) 4-[5-(5-Bromo-2-thienyl)-3-(difluoromethyl)-1H-pyrazol-1-yl]benzenesulfonamide
(29) 4-[5-(4-Thienyl)-3-(difluoromethyl)-1H-pyrazol-1-yl]benzenesulfonamide
(30) 4-[5-(4-[Trifluoromethyl]phenyl)-3-(difluoromethyl)-1H-pyrazol-1-yl]benzenesulfonamide
(31) 4-[5-(3,4-Dichlorophenyl)-3-(trifluoromethyl)-1H-pyrazol-1-yl]benzenesulfonamide
(32) 4-[5-(2,4-Dichlorophenyl)-3-(trifluoromethyl)-1H-pyrazol-1-yl]benzenesulfonamide
(33) 4-[5-Phenyl-3-(3-hydroxypropyl)-1H-pyrazol-1-yl]benzenesulfonamide
(34) 4-[5-(4-Fluorophenyl)-3-(3-hydroxypropyl)-1H-pyrazol-1-yl]benzenesulfonamide
(35) 4-[4-(Aminosulfonyl)phenyl]-5-(4-fluorophenyl) 1H-pyrazole]-3-propanoic acid
(36) 4,5-Dihydro-4-[3-trifluoromethyl]-1H-benz[g]indazol-1-yl]benzenesulfonamide
(37) 4-[5-(4-Chlorophenyl)-4-chloro-1H-pyrazol-1-yl]benzenesulfonamide
(38) 4-[5-(4-Chlorophenyl)-3-(trifluoromethyl)-4-chloro-1H-pyrazol-1-yl]benzenesulfonamide
(39) 4-[1-(4-Fluorophenyl)-3-(trifluoromethyl)-1H-pyrazol-5-yl]benzenesulfonamide
(40) 1-(2,4,6-Trichlorobenzoyl)-5-methoxy-2-methyl-3-indolyl acetic acid
(41) 1-(2,6-dichlorobenzoyl)-5-methoxy-2-methyl-3-indolyl acetic acid
(42) 3-(4-(Aminosulfonyl)phenyl)-2-(4-fluorophenyl)-5-(2-hydroxy-2-propyl)thiophene
(43) 3-(4-(Aminosulfonyl)phenyl)-2-(4-fluorophenyl) thiophene
(44) 3-(4-(Amino sulfonyl)phenyl)-2-(4-fluorophenyl)-5-(2-propyl)thiophene
(45) 3-(4-(Aminosulfonyl)phenyl)-2-cyclohexylthiophene
(46) 5-(4-Carboxyphenyl)-4-(4-(methylsulfonyl)phenyl) thiophene-2-carboxylic acid
(47) 4-(4-Fluorophenyl)-2-methyl-5-(4-(methylsulfonyl) phenyl)thiazole
(48) 2-(4-Fluorophenyl)-3-(4-methylsulfonyl)phenyl)-2-cyclopenten-1-one
(49) 4-(4-(Methylsulfonyl)phenyl-5-(4-fluorophenyl)-isothiazole
(50) 3-(4-Fluorophenyl)-4-(4-(methylsulfonyl)phenyl-2-(5H)-furanone
(51) 3-(4-Fluorophenyl)-4-(4-(aminosulfonyl)phenyl)-2-(2H)-furanone
(52) 3-(4-Fluorophenyl)-4-(4-(methylsulfonyl)phenyl)-furanone
(53) 5,5-Dimethyl-3-(4-fluorophenyl)-4-(4-methylsulfonyl-phenyl)-2-(5H)-furanone
(54) 2-((4-Aminosulfonyl)phenyl)-3-(4-fluorophenyl) thiophene
(55) 3-(2,4-Difluorophenyl)-4-(4-(methylsulfonyl)phenyl)-2-(5H)-furanone
(56) 3-(3,4-Difluorophenyl)-4-(4-(methylsulfonyl)phenyl)-2-(5H)-furanone
(57) 3-(2,6-Difluorophenyl)-4-(4-(methylsulfonyl)phenyl)-2-(5H)-furanone
(58) 3-(2,5-Difluorophenyl)-4-(4-(methylsulfonyl)phenyl)-2-(5H)-furanone
(59) 3-(3,5-Difluorophenyl)-4-(4-(methylsulfonyl)phenyl)-2-(5H)-furanone
(60) 3-(4-Bromophenyl)-4-(4-(methylsulfonyl)phenyl)-2-(5H)-furanone
(61) 3-(4-Chlorophenyl)-4-(4-(methylsulfonyl)phenyl)-2-(5H)-furanone
(62) 3-(4-Methoxyphenyl)-4-(4-(methylsulfonyl)phenyl)-2-(5H)-furanone
(63) 3-(Phenyl)-4-(4-(methylsulfonyl)phenyl)-2-(5H)-furanone
(64) 3-(2-Chlorophenyl)-4-(4-(methylsulfonyl)phenyl)-2-(5H)-furanone
(65) 3-(2-Bromo-4-fluorophenyl)-4-(4-(methylsulfonyl) phenyl)-2-(5H)-furanone
(66) 3-(2-Bromo-4-Chlorophenyl)-4-(4-(methylsulfonyl) phenyl)-2-(5H)-furanone
(67) 3-(4-Chloro-2-fluorophenyl)-4-(4-(methylsulfonyl) phenyl)-2-(5H)-furanone
(68) 3-(3-Bromo-4-fluorophenyl)-4-(4-(methylsulfonyl) phenyl)-2-(5H)-furanone
(69) 3-(3-Chlorophenyl)-4-(4-(methylsulfonyl) phenyl)-2-(5H)-furanone
(70) 3-(2-Chloro-4-fluorophenyl)-4-(4-(methylsulfonyl) phenyl)-2-(5H)-furanone
(71) 3-(2,4-Dichlorophenyl)-4-(4-(methylsulfonyl)phenyl)-2-(5H)-furanone
(72) 3-(3,4-Dichlorophenyl)-4-(4-(methylsulfonyl)phenyl)-2-(5H)-furanone
(73) 3-(2,6-Dichlorophenyl)-4-(4-(methylsulfonyl)phenyl)-2-(5H)-furanone
(74) 3-(3-Chloro-4-fluorophenyl)-4-(4-(methylsulfonyl) phenyl)-2-(5H)-furanone
(75) 3-(4-Trifluoromethylphenyl)-4-(4-(methylsulfonyl) phenyl)-2-(5H)-furanone
(76) 3-(3-Fluoro-4-methoxyphenyl)-4-(4-(methylsulfonyl) phenyl)-2-(5H)-furanone
(77) 3-(3-Chloro-4-methoxyphenyl)-4-(4-(methylsulfonyl) phenyl)-2-(5H)-furanone
(78) 3-(3-Bromo-4-methoxyphenyl)-4-(4-(methylsulfonyl) phenyl)-2-(5H)-furanone
(79) 3-(2-Fluorophenyl)-4-(4-(methylsulfonyl)phenyl)-2-(5H)-furanone

(80) 3-(4-Methylthiophenyl)-4-(4-(methylsulfonyl)phenyl)-2-(5H)-furanone
(81) 3-(3-Fluorophenyl)-4-(4-(methylsulfonyl)phenyl)-2-(5H)-furanone
(82) 3-(2-Chloro-6-fluorophenyl)-4-(4-(methylsulfonyl)phenyl)-2-(5H)-furanone
(83) 3-(3-Bromo-4-methylphenyl)-4-(4-(methylsulfonyl)phenyl)-2-(5H)-furanone
(84) 3-(4-Bromo-2-fluorophenyl)-4-(4-(methylsulfonyl)phenyl)-2-(5H)-furanone
(85) 3-(3,4-Dibromophenyl)-4-(4-(methylsulfonyl)phenyl)-2-(5H)-furanone
(86) 3-(4-Chloro-3-fluorophenyl)-4-(4-(methylsulfonyl)phenyl)-2-(5H)-furanone
(87) 3-(4-Bromo-3-fluorophenyl)-4-(4-(methylsulfonyl)phenyl)-2-(5H)-furanone
(88) 3-(4-Bromo-2-chlorophenyl)-4-(4-(methylsulfonyl)phenyl)-2-(5H)-furanone
(89) 3-(2-Naphthyl)-4-(4-(methylsulfonyl)phenyl)-2-(5H)-furanone
(90) 3-(7-Quinolinyl)-4-(4-(methylsulfonyl)phenyl)-2-(5H)-furanone
(91) 3-(3,4-Dichlorophenyl)-4-(4-(aminosulfonyl)phenyl)-2-(2H)-furanone
(92) 3-(3,4-Dichlorophenyl)-4-(4-(aminosulfonyl)phenyl)-2-(2H)-furanone
(93) 3-(3,4-Dichlorophenyl)-4-(4-(aminosulfonyl)phenyl)-2-(2H)-furanone
(94) 3-(3-Bromo-4-methoxyphenyl)-4-(4-(aminosulfonyl)phenyl)-2-(2H)-furanone
(95) 3-(4-(Methylsulfonyl)phenyl)-2-phenylbenzo[b]furan
(96) 3-(4-Methylsulfonyl)phenyl)-2-phenylbenzo[b]thiophene
(97) 3-(4-Methylsulfonyl)phenyl-2-phenylinden-1-one
(98) 2-(4-Fluorophenyl)-3-(4-(methylsulfonyl)phenyl)indole
(99) 3-(4-Fluorophenyl)-2-(4-(methylsulfonyl)phenyl)indole
(100) 2-(4-Fluorophenyl)-3-(4-(methylsulfonyl)phenyl)-4H-thieno[2,3-c]-furan-6-one
(101) 2-(3,4-Difluorophenyl)-3-(4-(methylsulfonyl)phenyl)-4H-thieno[2,3-c]-furan-6-one
(102) 2-(4-Fluorophenyl)-3-(4-(aminosulfonyl)phenyl)-4H-thieno[2,3-c]-furan-6-one
(103) 2-(3,4-Difluorophenyl)-3-(4-(aminosulfonyl)phenyl)-4H-thieno[2,3-c]-furan-6-one
(104) 3-(4-(Methylsulfonyl)phenyl)-2-phenyl-4,7-dihydrothieno[2,3-c]pyran-5-one
(105) 2-(4-(Methylsulfonyl)phenyl)-3-phenyl)-4H-thieno[2,3-c]furan-6-one
(106) 5-(4-(Methylsulfonyl)phenyl)-6-phenylimidazo[2,1-b]thiazole
(107) 2-Methyl-5-(4-(methylsulfonyl)phenyl)-6-phenylimidazo[2,1-b]thiazole
(108) 3-Methyl-5-(4-(methylsulfonyl)phenyl)-6-phenylimidazo[2,1-b]thiazole
(109) 2-Bromo-5-(4-(methylsulfonylphenyl)-6-phenylimidazo[2,1-b]thiazole
(110) 3-Trifluoromethyl-5-(4-(methylsulfonyl)phenyl)-6-phenylimidazo[2,1-b]thiazole
(111) 2,3-Dimethyl-5-(4-(methylsulfonyl)phenyl)-6-phenylimidazo[2,1-b]thiazole
(112) 5-(4-(Methylsulfonyl)phenyl)-6-(4-fluorophenyl) imidazo[2,1-b]thiazole
(113) 5-Phenyl)-6-(4-(methylsulfonyl)phenyl)-imidazo[2,1-b]thiazole
(114) 2-Chloro-5-(4-(methylsulfonyl)phenyl)-6-(4-chlorophen-yl)imidazo[2,1-b]thiazole
(115) 2,2-Dichloro-5-(4-(methylsulfonyl)phenyl)-6-(4-chlorophenyl)imidazo[2,1-b]thiazole
(116) 5-(4-(Methylsulfonyl)phenyl)-6-(imidazo[2,1-b]-1,3,4-thiadiazole
(117) 5-Phenyl-6-(4-(methylsulfonyl)phenyl)-imidazo[2,1-b]-1,3,4-thiadiazole
(118) 2-Methyl-5-(4-(methylsulfonyl)phenyl)-6-phenyl-imidazo[2,1-b]-1,3,4-thiadiazole
(119) 2-Methyl-5-phenyl-6-(4-methylsulfonyl)phenyl)-imidazo[2,1-b]-1,3,4-thiadiazole
(120) 5-(4-(Methylsulfonyl)phenyl)-6-(4-fluorophenyl)-imidazo[2,1-b]-1,3,4-thiadiazole
(121) 5-(4-(Methylsulfonyl)phenyl)-6-phenyl-1H-imidazo[2,1-b]-s-triazole
(122) 5-Phenyl-6-(4-(methylsulfonyl)phenyl)thiazolo[3,2-b]-1,3,4-triazole
(123) 2,3-Dihydro-5-(4-(methylsulfonyl)phenyl)-6-phenylimidazo[2,1-b]thiazole
(124) 2-[(4-Methylthio)phenyl]-1-biphenyl
(125) 1-Cyclohexene-2-(4'-methylsulfonylphenyl)benzene
(126) 3-(4'-Methylsulfonylphenyl)-4-phenylphenol
(127) 1-[2-(4-Methylsulfonylphenyl)phenyl]piperidine
(128) 1-[2-(4'-Methylsulfonylphenyl)phenyl]pyrrole
(129) 1-Phenoxy-2-(4'-methylsulfonylphenyl)benzene
(130) 5-(4-Fluorophenyl)-2-methoxy-4-[4-(methylsulfonyl)phenyl]-6-(trifluoromethyl)pyridine
(131) 2-Ethoxy-5-(4-fluorophenyl)-4-[4-(methylsulfonyl)phenyl]-6-(trifluoromethyl)pyridine
(132) 5-(4-Fluorophenyl)-4-[4-(methylsulfonyl)phenyl]-2-(2-propynyloxy)-6-(trifluoromethyl)pyridine
(133) 2-Bromo-5-(4-fluorophenyl)-4-[4-(methylsulfonyl)phenyl]-6-(trifluoromethyl)pyridine
(134) 3-[1-(p-Bromobenzyl)-5-methoxy-2-methylindol-3-yl]propanoic acid
(135) 3-[1-(p-Bromobenzyl)-5-methoxy-2-methylindol-3-yl]butanoic acid, sodium salt
(136) 2-Benzyl-3-[1-(p-bromobenzyl)-5-methoxy-2-methylindol-3-yl-propanoic acid
(137) 3-[1-(p-Bromobenzyl)-5-methoxy-2-methylindol-3-yl]-2,2-dimethylpropanoic acid
(138) 3-[1-(p-Bromobenzyl)-5-methoxy-2-methylindol-3-yl]-4,4,4-trifluorobutanoic acid, sodium salt
(139) trans-2-[1-(p-Bromobenzyl 5-methoxy-2-methylindol-3-yl]-cyclo-propanecarboxylic acid, sodium salt
(140) 3-[1-(p-Bromobenzyl)-5-methoxy-2-methylindol-3-yl]-hydroxy-2-methyl propanoic acid, sodium salt
(141) [1-(1-(p-Bromobenzyl)-5-methoxy-2-methylindol-3-yl]-cyclopropylacetic acid, sodium salt
(142) trans-(+)-2-[1-(p-Bromobenzyl)-5-methoxy-2-methylindol-3-yl]cyclopropanecarboxylic acid, sodium salt
(143) 3-[1-(p-Bromobenzyl)-5-methoxy-2-methylindol-3-yl]-2-methylpropanoic acid and sodium salt
(144) 3-[1-(p-Chlorobenzyl)-5-methoxy-2-methylindol-3-yl]-4,4,4-trifluorobutanoic acid and sodium salt
(145) syn-3-[1-(p-Bromobenzyl)-5-methoxy-2-methylindol-3-yl]-2-methylbutanoic acid
(146) anti-3-[1-(p-Bromobenzyl)-5-methoxy-2-methylindol-3-yl]-2-methylbutanoic acid and sodium salt
(147) 3-[5-(Bromo-1-(p-bromobenzyl)-2-methylindol-3-yl]butanoic acid and sodium salt
(148) (−)-3-[1-(p-Bromobenzyl)-5-methoxy-2-methylindol-3-yl]-butanoic acid and sodium salt
(149) (+)-3-[1-(p-Bromobenzyl)-5-methoxy-2-methylindol-3-yl]-butanoic acid and sodium salt (150) trans-(−)-2-[1-(p-Bromobenzyl)-5-methoxy-2-methylindol-3-yl]cyclopropanecarboxylic acid and sodium salt
(151) 3-[1-(p-Bromobenzyl)-2,5-dimethylindol-3-yl]propanoic acid
(152) 3-[5-(Bromo-1-(p-bromobenzyl)-2-methylindol-3-yl]propanoic acid
(153) 3-[1-(p-Bromobenzyl)-5-chloro-2-methylindol-3-yl)propanoic acid
(154) 3-[1-(p-Chlorobenzyl)-5-methoxy-2-methylindol-3-yl)-2-methylpropanoic acid
(155) Methyl 3-[1-(p-bromobenzyl)-5-methoxy-2-methylindol-3-yl)propanoate
(156) 3-[1-(p-Bromobenzyl)-5-methoxy-2-methylindol-3-yl)-3-methylbutanoic acid
(157) 5-Methanesulfonamido-6-(2,4-difluorophenylthio)-1-indanone
(158) 5-Methanesulfonamido-6-(2,4-dichlorophenoxy)-1-indanone
(159) 2-(4-Chlorophenyl)-4-hydroxy-1-[4-(methylsulfonyl)phenyl]-4-(trifluoromethyl)-4,5-dihydro-1H-imidazole
(160) 2-(4-Chlorophenyl)-1-[4-(methylsulfonyl)phenyl]-4-(trifluoromethyl)-1H-imidazole
(161) 1-(4-Fluorophenyl)-4-hydroxy-2-[4-(methylsulfonyl)phenyl]-4-(trifluoromethyl)-4,5-dihydro-1H-imidazole
(162) 1-(4-Fluorophenyl)-2-[4-(methylsulfonyl)phenyl]-4-(trifluoromethyl)-1H-imidazole
(163) 2-(4-Chlorophenyl)-1-[4-methylsulfonyl)phenyl]-4-methyl-1H-imidazole
(164) 2-(4-Chlorophenyl)-1-[4-methylsulfonyl)phenyl]-4-phenyl-1H-imidazole
(165) 2-(4-Chlorophenyl)-4-(4-fluorophenyl)-1-[4-(methylsulfonyl)phenyl]-1H-imidazole
(166) 4-(4-Bromophenyl)-2-(4-chlorophenyl)-1-[4-(methylsulfonyl)phenyl]-1H-imidazole
(167) 2-(4-Chlorophenyl)-1-[4-(methylsulfonyl)phenyl]-4-(2-naphthyl)-1H-imidazole
(168) 2-(4-Chlorophenyl)-1-[4-(methylsulfonyl)phenyl]-4-[4-(trifluoromethoxy)phenyl]-1H-imidazole
(169) 2,4-Bis(4-chlorophenyl)-1-[4-(methylsulfonyl)phenyl]-1H-imidazole
(170) 2-(4-Chlorophenyl)-4-(3-chlorophenyl)-1-[4-(methylsulfonyl)phenyl]-1H-imidazole
(171) 2-(4-Chlorophenyl)-4-(4-methoxyphenyl)-1-[4-(methylsulfonyl)phenyl]-1H-imidazole
(172) 2-(4-Chlorophenyl)-4-(3-fluorophenyl)-1-[4-(methylsulfonyl)phenyl]-1H-imidazole
(173) 2-(4-Chlorophenyl)-4-[(4-chlorophenoxy)methyl]-1-[4-(methylsulfonyl)phenyl]-1H-imidazole
(174) 2-(3-Chloro-4-methylphenyl)-1-[4-(methylsulfonyl)phenyl]-4-(trifluoromethyl)-1H-imidazole
(175) 5-[1-[4-(Methylsulfonyl)phenyl)-4-(trifluoromethyl)-1H-imidazole-2-yl]-1,3-benzodioxole
(176) 2-(3-Fluoro-4-methoxyphenyl)-1-[4-(methylsulfonyl)-phenyl-4-(trifluoromethyl)-1H-imidazole
(177) 2-(4-Chlorophenyl)-4-[(phenylthio)methyl]-1-[4-(methylsulfonyl)phenyl]-1H-imidazole
(178) 2-(4-Chlorophenyl)-4-[(N-methyl-N-phenylamino)methyl]-1-[4-(methylsulfonyl)phenyl]-1H-imidazole
(179) 2-(4-Chlorophenyl)-4-[2-quinolyl)methoxymethyl]-1-[4-(methylsulfonyl)phenyl]-1H-imidazole
(180) 2-(4-Chlorophenyl)-4-methoxymethyl-1-[4-(methylsulfonyl)phenyl]-1H-imidazole
(181) 2-(4-Fluorophenyl)-1-[4-(methylsulfonyl)phenyl]-4-trifluoromethyl-1H-imidazole
(182) 1-[4-(Methylsulfonyl)phenyl]-2-phenyl-4-trifluoromethyl-1H-imidazole
(183) 2-(3-Chloro-4-methoxyphenyl)-1-[4-(methylsulfonyl)phenyl]-4-trifluoromethyl-1H-imidazole
(184) 2-(4-Methylphenyl)-1-[4-(methylsulfonyl)phenyl]-4-trifluoromethyl-1H-imidazole
(185) 1-[4-(Methylsulfonyl)phenyl]-2-(4-trifluoromethylphenyl)-4-trifluomethyl-1H-imidazole
(186) 4-[2-(4-Chlorophenyl)-4-(trifluoromethyl)-1H-imidazol-1-yl]benzenesulfonamide
(187) 4-[2-(3-Chloro-4-methylphenyl)-4-(trifluoromethyl)-1H-imidazol-1-yl]benzenesulfonamide
(188) 3-[1-(4-Methylsulfonyl)phenyl]-4-trifluoromethyl-1H-imidazol-2-yl]pyridine
(189) 2-[1-(4-Methylsulfonyl)phenyl]-4-trifluoromethyl-1H-imidazol-2-yl]pyridine
(190) 4-[1-[4-(Methylsulfonyl)phenyl]-4-trifluoromethyl-1H-imidazol-2-yl]pyridine
(191) 2-Methyl-5-[1-[4-(methylsulfonyl)phenyl]-4-trifluoromethyl-1H-imidazol-2-yl]pyridine
(192) 2-Methyl-6-[1-[4-(methylsulfonyl)phenyl]-4-trifluoromethyl-1H-imidazol-2-yl]pyridine
(193) 5-Methyl-2-[1-[4-(methylsulfonyl)phenyl]-4-trifluoromethyl-1H-imidazol-2-yl]pyridine
(194) 4-Methyl-2-[1-[4-(methylsulfonyl)phenyl]-4-trifluoromethyl-1H-imidazol-2-yl]pyridine
(195) 2-Methoxy-5-[1-[4-(methylsulfonyl)phenyl]-4-trifluoromethyl-1H-imidazol-2-yl]pyridine
(196) 4-[2-(6-Methylpyridin-3-yl)-4-(trifluoromethyl)-1H-imidazol-1-yl]benzenesulfonamide
(197) 4-[2-(6-Methylpyridin-2-yl)-4-(trifluoromethyl)-1H-imidazol-1-yl]benzenesulfonamide
(198) 3-Methyl-5-[1-[4-(methylsulfonyl)phenyl]-4-(trifluoromethyl)-1H-imidazol-2-yl]pyridine
(199) 4-[2-(4-Methylpyridin-2-yl)-4-(trifluoromethyl)-1H-imidazol-1-yl]benzenesulfonamide
(200) 2-[1-[4-(Methylsulfonyl)phenyl]-4-(trifluoromethyl)-1H-imidazol-2-yl]thiophene
(201) 3-[1-[4-(Methylsulfonyl)phenyl]-4-(trifluoromethyl)-1H-imidazol-2-yl]thiophene
(202) 4-[2-(5-Methylpyridin-3-yl)-4-(trifluoromethyl)-1H-imidazol-1-yl]benzenesulfonamide
(203) 2-Methyl-3-[1-[4-(methylsulfonyl)phenyl]-4-(trifluoromethyl)-1H-imidazol-2-yl]thiophene
(204) 4-[2-(2-Methylpyridin-3-yl)-4-(trifluoromethyl)-1H-imidazol-1-yl]benzenesulfonamide
(205) 4-[2-Pyridin-3-yl)-4-(trifluoromethyl)-1H-imidazol-1-yl]benzenesulfonamide The synthesis of compounds 1–39 is disclosed in Talley et al. U.S. Pat. No. 5,466,823. The synthesis of compounds 40 and 41 is disclosed in Black et al. U.S. Pat. No. 5,436,265. The synthesis of compounds 42–94 is disclosed in Ducharme et al. U.S. Pat. No. 5,474,995. The synthesis of compounds 95–105 is disclosed in Prasit et al. U.S. Pat. No. 5,521,213. The synthesis of compounds 106–123 is disclosed in Gauthier et al. U.S. Pat. No. 5,552,422. The synthesis of compounds 124–129 is disclosed in Batt U.S. Pat. No. 5,593,994. The synthesis of compounds 130–133 is disclosed in Lee U.S. Pat. No. 5,596,008. The synthesis of compounds 134–156 is disclosed in Lau et al. U.S. Pat. No. 5,604,253. The synthesis of compounds 157 and 158 is disclosed in Guay et al. U.S. Pat. No. 5,604,260. The synthesis of compounds 159–205 is disclosed in Khanna et al. U.S. Pat. No. 5,616,601.

Other selective inhibitors of cyclooxygenase-2 and their synthesis are taught in Examples 2–108, 110–129, 131–150, 152, 301–312, and 401–413 of Batt et al. U.S. Pat. No. 5,593,994, the disclosure of which is incorporated herein by reference. Still other selective inhibitors of cyclooxygenase-2 and their synthesis are taught in Examples 1–11, 13–16, and 18–25 of Guay et al. U.S. Pat. No. 5,604,260, the disclosure of which is incorporated herein by reference. Still other selective inhibitors of cyclooxygenase-2 and their synthesis are taught in Examples 1–13 including Examples 1a–1p and 4a–4h of Talley et al. U.S. Pat. No. 5,633,272, the disclosure of which is incorporated herein by reference. Still other selective inhibitors of cyclooxygenase-2 are taught in Examples 1–131 of Lau et al. U.S. Pat. No. 5,639,780, the disclosure of which is incorporated herein by reference. Still other selective inhibitors of cyclooxygenase-2 are taught in Examples 1–6 of Talley et al. U.S. Pat. No. 5,643,933, the disclosure of which is incorporated herein by reference. Still other selective inhibitors of cyclooxygenase-2 are taught in Examples 1–4 of Lau et al. U.S. Pat. No. 5,510,368, the disclosure of which is incorporated herein by reference.

Preferred inhibitors of cyclooxygenase-2 for use herein are 4-[5-(4-chlorophenyl)-3-(trifluoromethyl)-1H-pyrazol-1-yl]benzenesulfonamide which is compound (1) set forth above and 4-[5-(4-methylphenyl)-3-(trifluoromethyl)-1H-pyrazol-1-yl]benzenesulfonamide which is compound (4) set forth above; it is believed the latter compound is celicoxib (Trade name Celebrex). Another preferred selective inhibitor of cyclooxygenase-2 is vioxx which is MK-0966. Other preferred inhibitors of cyclooxygenase-2 for use in this embodiment are those described hereinafter in connection with the third embodiment herein.

The dosage of inhibitor of cyclooxygenase-2 for the method of the first embodiment herein is a cyclooxygenase-2 inhibiting amount which is a therapeutically effective amount. In general, the dosage for the first embodiment herein ranges from 0.1 to 30 mg/kg. The dosages for any particular agent will vary within said range. For compound (1) referred to above, the dosage preferably ranges from 3 to 12 mg/kg. The administration is preferably chronic treatment, i.e., carried out indefinitely.

The route of administration for the inhibitors of cyclooxygenase-2 for the first embodiment herein is preferably oral but other routes of administration, e.g., parenteral such as intravenous, are also useful.

We turn now to the second embodiment herein, which is a method of treating a patient with a virus-caused liver disease with a cyclooxygenase-2 inhibiting amount of a selective inhibitor of cyclooxygenase-2 and a therapeutic amount of an anti-viral drug where the cyclooxygenase-2 inhibitor is an adjunct to the anti-viral therapy to increase the effectiveness thereof.

For the second embodiment herein, the virus-cause liver diseases include, for example, chronic viral hepatitis B and chronic viral hepatitis C.

For the second embodiment herein, the inhibitors of cyclooxygenase-2 that are useful are the same as those for the first embodiment herein and the dosage regimen and routes of administration are the same as for the first embodiment.

The anti-viral drugs are the same as those used conventionally for the disorder treated, and the dosages and routes of administration are those conventional for the disorder treated. For example, for chronic hepatitis B, various interferons, e.g., recombinant and natural alpha interferons, are administered parenterally and for chronic hepatitis C, interferon alpha-2b is administered subcutaneously (3 MU three times a week for six months). Other anti-viral compounds for use in the second embodiment herein include, for example, acyclovir, adenine arabinoside, and ribavirin, used, for example in conventional dosages. Combinations of agents, e.g., a combination of interferon and ribavirin, may be used with the selective inhibitor of cyclooxygenase-2.

We turn now to the third embodiment herein which is directed to selective inhibitors of cyclooxygenase-2 which directly inhibit the enzyme cyclooxygenase-2 and which also inhibit the synthesis of cyclooxygenase-2 protein and which have antioxidant properties.

The cyclooxygenase-2 inhibitors for this third embodiment preferably contain phenyl group with two or more substituents selected from the group consisting of hydroxy and $C_{1-4}$-alkoxy (e.g., methoxy) on the phenyl. Such compounds are embraced by generic description in various patents but no species of selective cyclooxygenase-2 inhibitor containing phenyl group with two or more hydroxy or alkoxy substituents is disclosed in any of said patents. The patents referred to are: Talley et al. U.S. Pat. No. 5,643,933; Talley et al. U.S. Pat. No. 5,633,272; Khanna et at U.S. Pat. No. 5,616,601; Lee U.S. Pat. No. 5,596,008; Batt et al. U.S. Pat. No. 5,593,994; and Adams et al. U.S. Pat. No. 5,593,992.

Specific compounds for the third embodiment herein include, for example, 4-[5-methyl-3-[[(2,3-hydroxy)phenoxy]methyl]-1H-pyrazol-1-yl]benzenesulfonamide and 4-methyl-5-(4-methylsulfonyl)phenyl-2-[(2,3-hydroxyphenoxy)methyl]oxazole and the corresponding compounds where methoxy or ethoxy replaces hydroxy. 4-[5-Methyl-3-[[(2,3-hydroxy)phenoxy]methyl]-1H-pyrazol-1-yl]benzenesulfonamide has the structure

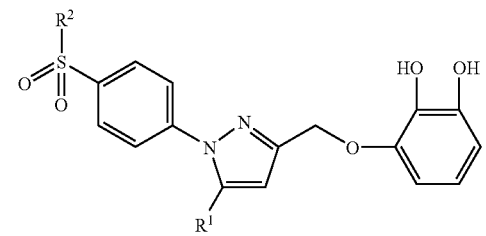

where $R^1$ is methyl and $R_2$ is $NH_2$. 4-(Methyl)-5-(4-methylsulfonyl)phenyl-2-[(2,3-hydroxyphenoxy)methyl]oxazole has the structure

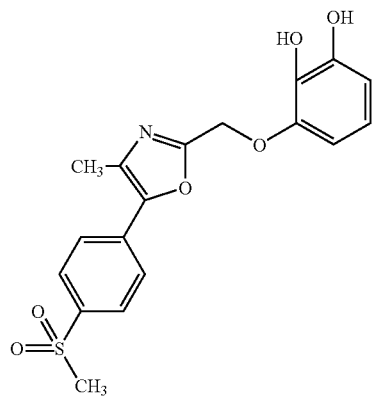

These compounds are embraced by broad disclosure in Talley et al. U.S. Pat. No. 5,643,933 but are not specifically disclosed therein. These compounds can be made analogously to Scheme XXII in U.S. Pat. No. 5,643,933 by reacting 2,3-dihydroxybenzyl bromide, where the hydroxy groups are protected by conventional techniques (for example, as described in E. Haslam, "Protection of Phenols and Catechols", pages 145–182 in Protective Groups in Organic Chemistry, McOmie, J. F. W., editor, Plenum Press, London (1973), with alcohol corresponding to the product sought, in the presence of base, and deprotecting, and in the case of the methoxy or ethoxy compounds with alkoxy substituents in phenyl moiety, replacing the hydroxy substituents with alkoxy. Alternatively, these compounds can be made by reacting said alcohol with mesyl chloride to yield the unstable mesylate and then reacting with appropriate trihydroxyphenol. These compounds directly inhibit the cyclooxygenase-2 enzyme and also inhibit the synthesis of cyclooxygenase-2.

The selective inhibitors of cyclooxygenase-2 for the third embodiment herein have utility as broad spectrum anti-inflammatory agents for treating inflammation and inflammation-associated disorders mediated by cyclooxygenase-2 such as arthritis, inflammatory bowel disease, diabetes, Alzheimer's disease, pancreatitis, inflammatory vascular and ocular disorders, and liver disease (as described in conjunction with the first embodiment herein). They also have utility in preventing or treating cancer. The dosages are generally those set forth for selective inhibitors of cyclooxygenase-2 in the first embodiment herein. The route of administration is preferably oral although other routes of administration, e.g., parenteral, such as intravenous, may also be used.

The selective inhibitors of cyclooxygenase-2 of the third embodiment herein have improved anti-inflammatory efficacy compared to selective inhibitors of cyclooxygenase-2 which do not inhibit the synthesis of cyclooxygenase-2 protein.

The three embodiments described above are illustrated in the following examples.

EXAMPLE I

A patient with alcoholic hepatitis is admitted to a hospital complaining of nausea and upper abdominal pain. Liver function test results are total bilirubin of 4.0 mg/dl, direct bilirubin of 3.1 mg/dl, ALT of 100 IU/L, AST of 120 IU/L and prothrombin time of 15.1 seconds.

Treatment is carried out by administration of 4-[5-(4-chlorophenyl)-3-(trifluoromethyl)-1H-pyrazol-1-yl]benzenesulfonamide at a dosage of 6 mg/kg by oral route of administration, daily.

At the end of three weeks, the nausea and upper abdominal pain have resolved. Each of the blood tests has improved.

The same result is obtained when the drug administered is 4-[5-(4-methylphenyl)-3-(trifluoromethyl)-1H-pyrazol-1-yl]benzenesulfonamide at a dosage of 6 mg/kg by oral route of administration daily.

EXAMPLE II

The patient is a 45-year old female with new onset nausea, loss of appetite and right upper quadrant tenderness. She is noted to have elevated liver chemistries. Serologic workup is notable for positive antinuclear and antismooth muscle antibodies. She is considered to have autoimmune hepatitis. Liver biopsy is consistent with this diagnosis. Treatments with 6 mg/kg oral 4-[5-(4-chlorophenyl)-3-(trifluoromethyl)-1H-pyrazol-1-yl]benzene-sulfonamide for two months, results in resolution of symptoms. The patient is subsequently maintained on an oral dose of 6 mg/kg of the same drug.

The same result is obtained when the drug administered is 4-[5-(4-methylphenyl)-3-(trifluoromethyl)-1H-pyrazol-1-yl]benzenesulfonamide at an oral dose of 6 mg/kg.

EXAMPLE III

A patient having symptoms of malaise, anorexia and fatigue, has persistently elevated liver function tests. A blood test confirms the diagnosis of chronic viral hepatitis C.

The patient is treated by oral administration of 4-[5-(4-chlorophenyl)-3-(trifluoromethyl)-1H-pyrazol-1-yl]benzene-sulfonamide at a dose of 6 mg/kg, daily for 12 months and also with subcutaneous interferon alpha-2b at a dose of 3 MU three times a week for six months, resulting in sustained normalization of liver enzymes.

The same result is obtained when the cyclooxygenase-2 inhibitor is 4-[5-(4-methylphenyl)-3-(trifluoromethyl)-1H-pyrazol-1-yl]benzenesulfonamide at an oral dose of 6 mg/kg and the anti-viral drug is subcutaneous interferon alpha-2b at a dose of 3 Mu three times a week for six months.

EXAMPLE IV

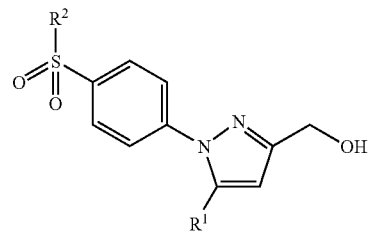

where $R^1$ is methyl and $R^2$ is $NH_2$ is reacted with 2,3-dihydroxybenzylbromide where the hydroxyls are protected, under basic conditions ($K_2CO_3$), and then deprotecting is carried out to produce 4-[5-methyl-3-[(2,3-hydroxy)phenoxy]methyl]-1H-pyrazol-1-yl]benzenesulfonamide. The product has the structure

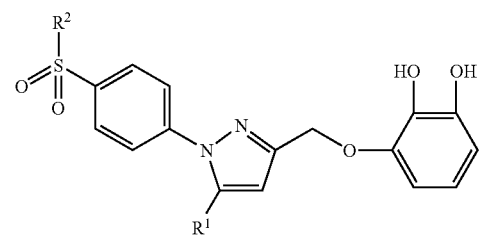

where $R^1$ is methyl and $R^2$ is $NH_2$. The starting material is made by the reaction to produce compound 78 in Scheme XVII depicted in Talley et al. U.S. Pat. No. 5,643,933.

Many variations of the above will be obvious to those skilled in the art. Thus, the invention is defined by the claims.

The invention claimed is:

1. A method of treating a patient affected with liver disease selected from the group consisting of chronic viral hepatitis B, chronic viral hepatitis C, alcoholic liver injury and nonalcoholic steatohepatitis, comprising administering to said patient a cyclooxygenase-2 inhibiting amount of a selective inhibitor of cyclooxygenase-2.

2. The method of claim 1, wherein the selective inhibitor of cyclooxygenase-2 is 4-[5-(4-chlorophenyl)-3-(trifluoromethyl)-1H-pyrazol-1-yl]benzenesulfonamide.

3. The method of claim 1, wherein the selective inhibitor of cyclooxygenase-2 is 4-[5-(4-methylphenyl)-3-(trifluoromethyl)-1H-pyrazol-1-yl]benzenesulfonamide.

4. The method of claim 1 wherein the selective inhibitor of cyclooxygenase-2 directly inhibits the enzyme cyclooxygenase-2 and also inhibits the synthesis of cyclooxygenase-2 protein and contains phenyl group with two or more substituents selected from the group consisting of hydroxy and $C_{1-4}$-alkoxy on the phenyl group.

* * * * *